(12) United States Patent
Liu et al.

(10) Patent No.: US 10,098,571 B2
(45) Date of Patent: Oct. 16, 2018

(54) DIGESTIVE TRACT PATENCY CAPSULE

(71) Applicant: Side Liu, Guangzhou (CN)

(72) Inventors: Side Liu, Guangzhou (CN); Wei Zhang, Guangzhou (CN); Zelong Zhang, Guangzhou (CN); Yangzhi Xu, Guangzhou (CN)

(73) Assignee: Side Liu, Guangzhou, GD (CN)

( * ) Notice: Subject to any disclaimer, the term of this patent is extended or adjusted under 35 U.S.C. 154(b) by 338 days.

(21) Appl. No.: 14/898,142

(22) PCT Filed: May 9, 2014

(86) PCT No.: PCT/CN2014/077093
§ 371 (c)(1),
(2) Date: Dec. 14, 2015

(87) PCT Pub. No.: WO2015/003529
PCT Pub. Date: Jan. 15, 2015

(65) Prior Publication Data
US 2016/0213285 A1     Jul. 28, 2016

(30) Foreign Application Priority Data

Jul. 8, 2013   (CN) .......................... 2013 1 0285406
Sep. 11, 2013  (CN) .......................... 2013 1 0413545

(51) Int. Cl.
*A61B 5/00*     (2006.01)
*A61B 5/107*    (2006.01)
*A61M 31/00*    (2006.01)

(52) U.S. Cl.
CPC .......... *A61B 5/1076* (2013.01); *A61B 5/4255* (2013.01); *A61B 5/6861* (2013.01); *A61M 31/005* (2013.01)

(58) Field of Classification Search
CPC . A61K 9/4808; A61M 31/002; A61M 31/005; A61B 5/103; A61B 5/1076; A61B 5/6861; A61B 5/4225
See application file for complete search history.

(56) References Cited

U.S. PATENT DOCUMENTS

| | | | |
|---|---|---|---|
| 6,368,629 B1 * | 4/2002 | Watanabe | A61K 9/2826 424/468 |
| 2009/0118579 A1 * | 5/2009 | Duerschinger | A61K 9/4808 600/109 |

(Continued)

*Primary Examiner* — Max Hindenburg
(74) *Attorney, Agent, or Firm* — George G. Wang; Bei & Ocean

(57) ABSTRACT

Disclosed is a digestive tract patency capsule, comprising an outer membrane (2) and a supporting material (1) which is soluble in digestive juices. The outer membrane (2) is a sealed soft capsule body made from a sustained-release enteric material, and the dissolution time of the outer membrane (2) is greater than the normal emptying time of the human digestive tract. The cavity of the capsule body of the outer membrane (2) is provided with an indicator (5) which can be absorbed by the body and enables the discharged urine to change color. The supporting material (1) is provided in the cavity of the capsule body of the outer membrane (2) to support the outer membrane (2) in a capsule form. The digestive tract patency capsule can safely and effectively check the feasibility of performing a capsule endoscopic examination on a user. The digestive tract patency capsule can predict the feasibility of a capsule endoscopic examination and is taken before performing a capsule endoscopic examination on a patient, thus safely, simply and effectively providing a good basis for the determination of whether a capsule endoscopic examination should be performed for a clinician.

2 Claims, 9 Drawing Sheets

(56) References Cited

U.S. PATENT DOCUMENTS

2009/0299231 A1* 12/2009 Takizawa ............... A61B 1/041
                                                      600/593
2011/0174653 A1*  7/2011 Schwarz ................ A61J 3/071
                                                      206/461

* cited by examiner

DIGESTIVE TRACT PATENCY CAPSULE

CROSS-REFERENCE TO RELATED APPLICATIONS

This application claims priority from CN Application No. 201310285406.4, filed Jul. 8, 2013, CN Application No. 201310413545.0, filed Sep. 11, 2013, and PCT Application No. PCT/CN2014/077093, filed May 9, 2014, the contents of which are incorporated herein in the entirety by reference.

FIELD OF THE INVENTION

The present invention relates to a medical instrument, and particularly relates to a digestive tract patency capsule.

BACKGROUND OF THE INVENTION

The capsule endoscopy (CE) with the full name of "intelligent capsule digestive-tract endoscopy system" is a non-invasive diagnosis technique developed in recent years, and was approved by the U.S. Food and Drug Administration (FDA) in 2001 for examination of small intestinal diseases. The CE has the advantages of being easily operated, being convenient for examination, being noninvasive, having no pain, having no cross-infection, having no influence on normal work of the patient and the like. By 2009, more than 0.75 million people had undergone the CE examination. Currently, the CE is mainly used for diagnosis of diseases such as obscure gastrointestinal bleeding, Crohn's disease, small intestine tumor and the like, and with the technology development in recent years, a CE used for examination of oesophagus and colon gradually appears, which further widens the application range of the CE and provides great aids for the gastroenterologist. Also, a magnetic assisted capsule endoscopy system capable of observing gastric lesions has already been reported by a study.

However, capsule retention caused by luminal stenosis due to tumors or various diseases is a common adverse event of CE. The small intestine has a smaller diameter as compared with the stomach and colon, and thus the retention of capsule is more likely in the case of stenosis of small intestine. Since the CE is non-degradable, the CE must be removed if retention thereof occurs, otherwise a serious consequence will be caused. Moreover, unlike the stomach and colon, it is difficult to remove the capsule if retention thereof occurs, and sometimes even an laparotomy is needed, thereby bringing great agony to the patient.

Therefore, it is especially important to prevent capsule retention. Currently, the clinician mostly screens patients for CE examination based on medical histories thereof initially, and then further determines whether an intestinal stenosis exists through a contrast examination. However, the accuracy rate of this method is poor, wherein missed diagnosis of some patients occurs, and some patients with intestinal stenosis as determined through contrast examination still can complete the CE examination. Some intestinal stenoses are in the type of functional stenosis, which still can deform to allow pass of the capsule when the CE passes therethrough. The CE examination result of such a patient is often positive, which provides an important basis for diagnosis of the patient. Therefore, there is a need for us to find a more accurate method for judging whether the intestinal condition is suitable for CE examination, which is noninvasive, safe and reliable, neither making the patient be subjected to an unnecessary examination nor causing the patient to lose a good opportunity for definite diagnosis of diseases.

In 2006, Xi-Tian Pi et al. invented a sustained-release tablet for detecting digestive-tract emptying and a process for preparing the same; and in 2010, Elisha Rahinovitz et al. invented a degradable capsule for evaluating whether an intestinal stenosis exists before the CE examination. Both of the aforementioned patency capsules have a similar size to a normal CE, which are taken by a patient before the CE examination, and can be successfully discharged from the body if the digestive-tract of the patient is unobstructed, otherwise the capsules are degraded by themselves with no residue. Also, whether the capsule still exists in the body and the approximate position of the capsule may be determined by X-ray positioning. However, these methods are still lack of accuracy; certain harmful radiation to human bodies is caused by the ray; and the methods are a bit complicated as requiring the aid of an X-ray apparatus.

SUMMARY OF THE INVENTION

The object of the present invention is to provide a digestive tract patency capsule capable of safely and effectively determining the feasibility of performing a CE examination on a user.

The object of the present invention is achieved by the following technical measures.

A digestive tract patency capsule is provided, which is characterized in that the digestive tract patency capsule includes an outer membrane and a supporting material which is soluble in digestive juices. The outer membrane is a sealed soft capsule body made from a sustained-release enteric material, and the dissolution time of the outer membrane is greater than the normal emptying time of the human digestive tract. The cavity of the capsule body of the outer membrane is provided with an indicator which can be absorbed by the body and enables the discharged urine to change color. The supporting material is provided in the cavity of the capsule body of the outer membrane to support the outer membrane in a capsule form.

As an improvement of the present invention, the digestive tract patency capsule also includes an envelope disposed in the outer membrane. The envelope is a capsule body made from a material only soluble in the small intestine. The capsule body is provided with a through hole connected to the cavity of the capsule body, and a sealing interlayer is installed in the inner wall of the capsule body. The indicator is accommodated in the sealing interlayer of the envelope, and the cavity of the capsule body of the envelope is filled with the supporting material, such that both of the outer membrane and the envelope are supported in a capsule form.

In order to improve the structure stability of the patency capsule and as an improvement of the aforementioned solution, the shape of the envelope is adapted to that of the outer membrane, and the envelope closely fits against the inner wall of the outer membrane after being filled with the supporting material, wherein the envelope is provided with two through holes respectively opened on two curved end terminals of the capsule body.

As an improvement of the present invention, the digestive tract patency capsule also includes an envelope disposed in the outer membrane. The envelope is a sealed capsule body made from a material only soluble in the small intestine. The indicator is accommodated in the sealed cavity of the envelope, and the sealed cavity of the envelope is also filled with the supporting material, such that both the outer membrane and the envelope are supported in a capsule form.

In order to improve the structure stability of the patency capsule and as an improvement of the aforementioned solution, the shape of the envelope is adapted to that of the outer membrane, and the envelope closely fits against the inner wall of the outer membrane after being filled with the supporting material.

As an implementation of the present invention, the envelope is a protein membrane or a starch-based membrane.

In order to reduce the breakdown time of the patency capsule when it is incarcerated at the stenosis in the digestive tract, for avoiding discomfort of the user caused by too long retention time of the patency capsule, and for further improving the safety of the patency capsule, the outer membrane is provided with a through hole which is blocked by a hole plug for sealing the outer membrane. The hole plug is made from a sustained-release enteric material which has a dissolution time between the normal emptying time of the human digestive tract and the dissolution time of the outer membrane.

Since the capsule advancing in the digestive tract generally has a gesture that the end terminal of the capsule is located at the forefront, in order to ensure that the hole plug is dissolved by the digestive juices at first time so as to reduce discomfort of the patient, the two curved end terminals of the capsule body of the outer membrane are both provided with through holes which are respectively blocked by hole plugs.

In order to ensure sealing of the outer membrane and as an improvement of the present invention, the material of the outer membrane is polylactic acid, microcrystalline cellulose or polyvinyl pyrrolidone; the material of the hole plug is microcrystalline cellulose, glyceryl behenate, polyvinyl pyrrolidone, hydroxypropyl methyl cellulose or lactose. The hole plug is adaptively embedded in the through hole and is tightly connected to the outer membrane via a biological glue or a UV glue.

As an implementation of the present invention, the indicator is a colored contrast agent.

As an implementation of the present invention, the supporting material is gelatin, lactose or starch which has an adjustable weight ratio so as to stimulate the actual weight of a capsule endoscopy (CE).

As compared with the prior art, the present invention has the following beneficial effects:

First, in the digestive tract patency capsule of the present invention, the outer membrane is supported in a capsule form by the supporting material, and the ratio of the supporting material is adjusted to stimulate the actual weight of the CE, such that the size, weight and appearance of the patency capsule are substantially the same as those of the CE, thereby fully stimulating the condition of the CE in the human body.

Second, the digestive tract patency capsule of the present invention is provided with an outer membrane made from a sustained-release enteric material, the dissolution time of the outer membrane is greater than the normal emptying time of the human digestive tract, and the cavity of the capsule body of the outer membrane is provided with an indicator which can be absorbed by the body and enables the discharged urine to change color, wherein if no stenosis exists in the digestive tract of the user, the patency capsule remains stable in the human body until the capsule is completely discharged from the body in the feces after a normal emptying time of the human digestive tract, so that the process of the CE passing the human digestive tract is fully stimulated without any influence on the human body, and meanwhile, it shows that it is feasible to perform the CE examination on the user; and if a luminal stenosis exists in the small intestine or large intestine of the user and thus the digestive tract patency capsule is incarcerated in the small intestine or large intestine, then the outer membrane is dissolved by the digestive juices to release the indicator contained therein, such that the color of the urine of the user is changed to blue to alarm the user that a luminal stenosis exists in his/her small intestine or large intestine and thus the CE examination is not feasible, and also while the indicator is released, the digestive juices further dissolve the supporting material and thus the patency capsule is broken down to allow the remaining material to pass through the stenosis, thereby reducing the discomfort of the user caused by the retention of the patency capsule; therefore the present invention can safely detect the condition of luminal stenosis in the small intestine or large intestine of the user and predict the feasibility of the CE examination, and is taken before performing the CE examination on the patient, thus safely, simply and effectively providing a good basis for the determination of whether the CE examination should be performed for a clinician, and the patency capsule of the present invention does not need an auxiliary examination with the X ray so that the user can use the patency capsule to perform a safe and effective examination independently outside the hospital.

Third, the digestive tract patency capsule of the present invention is additionally provided with an envelope made from a material only soluble in the small intestine, wherein the envelope is preferably designed as a capsule body provided with a through hole in communication with the cavity of the capsule body, a sealing interlayer is installed in the inner wall of the capsule body, the indicator is accommodated in the sealing interlayer of the envelope, and the cavity of the capsule body of the envelope is filled with the supporting material, such that if a luminal stenosis exists in the small intestine of the user and thus the digestive tract patency capsule is incarcerated at this location, then the digestive juices in the small intestine can penetrate the outer membrane to dissolve the envelope and the supporting material at the same time so as to release the indicator contained in the envelope into the small intestine, and thus the color of the urine of the user is changed to blue to alarm the user that a luminal stenosis exists in his/her small intestine and thus the CE examination is not feasible, and after the supporting material is finally dissolved completely, the entire digestive tract patency capsule is broken down, and the remaining material of the patency capsule may pass through the stenosis as an amorphous substance and is finally discharged from the body through the anus; additionally if the digestive tract patency capsule is retained in the large intestine, since the digestive juices of the large intestine cannot dissolve the envelope, only the supporting material is dissolved, and thus after the supporting material is finally dissolved completely, the capsule structure of the digestive tract patency capsule is broken down while the outer membrane and the envelope can be remained intact, and the outer membrane and the envelope, together with the indicator contained in the envelope can pass through the stenosis and are finally discharged from the body through the anus, wherein for such a case, the indicator is not released and thus no influence is caused to the examination result; therefore, the present invention can detect the condition that a stenosis exists in the small intestine of the user by positioning.

Fourth, the outer membrane of the digestive tract patency capsule of the present invention is provided with a through hole which is blocked with a hole plug, and the hole plug is made from a sustained-release enteric material having a dissolution time between the normal emptying time of the human digestive tract and the dissolution time of the outer membrane, such that when the patency capsule is incarcerated at the stenosis, the digestive juices can first dissolve the hole plug to penetrate the outer membrane, and thus the patency capsule is facilitated to be broken down as early as possible so as to enable the remaining material to pass the stenosis, thereby reducing the breakdown time of the patency capsule incarcerated at the stenosis in the digestive tract, avoiding discomfort of the user caused by long retention time of the patency capsule, and further improving the safety of the patency capsule.

BRIEF DESCRIPTION OF THE DRAWINGS

The present invention is further illustrated below in details through the specific embodiments in conjunction with accompanying drawings.

DETAILED DESCRIPTION OF PARTICULAR EMBODIMENTS OF THE INVENTION

The First Embodiment

Figure 1:
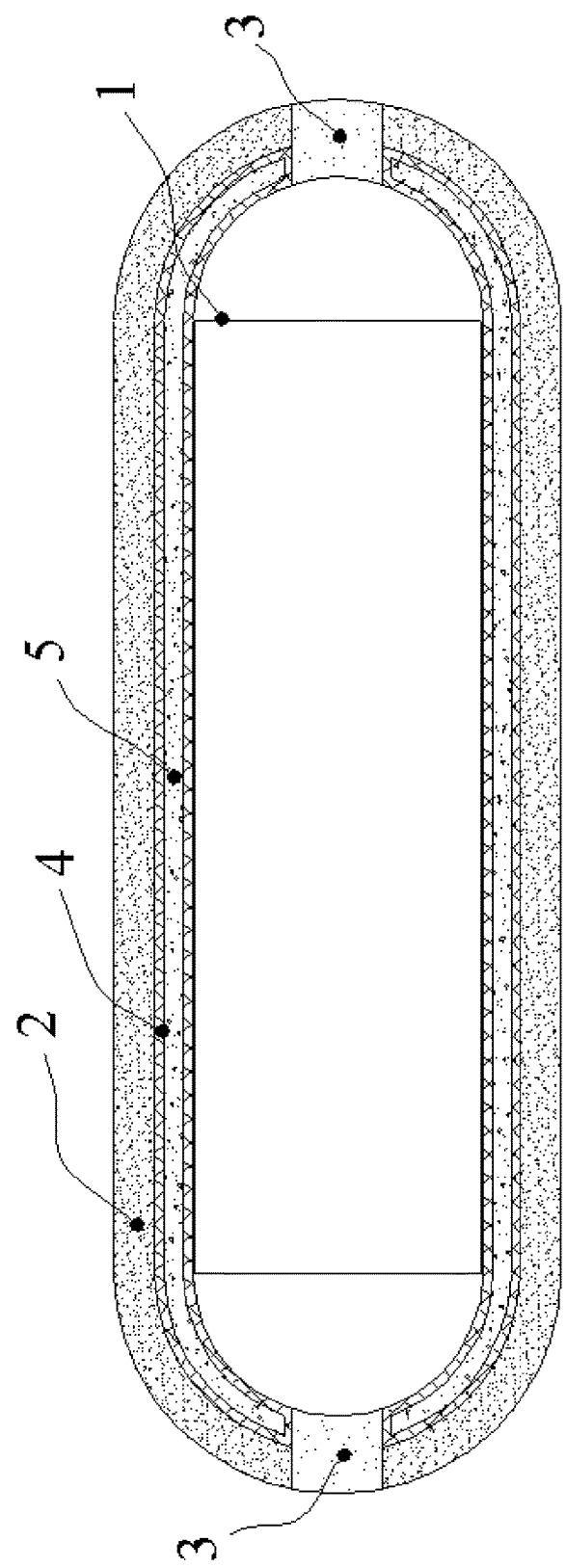
FIG. 1 is a schematic structure view of a digestive tract patency capsule according to a first embodiment of the present invention.

As shown in FIG. 1, the digestive tract patency capsule according to the first embodiment of the present invention is formed by an outer membrane 2, two hole plugs 3, an envelope 4, an indicator 5 and a supporting material 1.

The outer membrane 2 is made from a degradable material with great biocompatibility, such as a soft capsule body made from a sustained-release enteric material. Two curved end terminals of the capsule body of the outer membrane 2 are both provided with through holes. By reasonably choosing the composition and ratio of the sustained-release enteric material, the dissolution time of the outer membrane 2 is set as greater than the normal emptying time of the human digestive tract, wherein since the fastest normal emptying time of the human digestive tract is about 12 hours and the average time is about 24 hours, the dissolution time of the outer membrane 2 is preferably 48-72 hours. The material of the outer membrane 2 of the present invention is preferably polylactic acid, microcrystalline cellulose or polyvinyl pyrrolidone.

The two through holes of the aforementioned outer membrane 2 are respectively blocked by two hole plugs 3. The hole plugs 3 are adaptively embedded in the through holes and are tightly connected to the outer membrane 2 through a biological glue or a UV glue, such that the outer membrane 2 and the hole plugs 3 form a sealed integral body. The hole plugs 3 are also made from a sustained-release enteric material. By reasonably choosing the composition and ratio of the sustained-release enteric material, the dissolution time of the hole plugs 3 is between the normal emptying time of the human digestive tract and the dissolution time of the outer membrane 2, depending flexibly on actual clinical situations. The material of the hole plugs 3 of the present invention is preferably microcrystalline cellulose, glyceryl behenate, polyvinyl pyrrolidone, hydroxypropyl methyl cellulose or lactose. The hole plugs 3 are preferably set as being substantially stable during a time period of 30-48 hours and are completely dissolved after 48-72 hours.

The envelope 4 is a capsule body has a shape adapted to that of the outer membrane 2. Two curved end terminals of the capsule body are both provided with through holes in communication with the cavity of the capsule body. A sealing interlayer is installed in the inner wall of the capsule body, and the indicator 5 is accommodated in the sealing interlayer. The envelope 4 is installed in the outer membrane 2. The aforementioned two hole plugs 3 are adaptively embedded in two through holes of the envelope 4 respectively; wherein the envelope 4 is made from a material only soluble in the small intestine, which may be a protein membrane or starch-based membrane, containing essential components of vegetable proteins, hydroxyethyl acrylate or glycerinum which is used as a plasticizer, aldehyde cross-linking agent or a starch material, and characterized by being waterproof, oil-proof and edible, having certain mechanical strength, remaining stable in the digestive juices of the large intestine and remaining stable under a mechanical pressure caused by intestinal tract movement. The envelope 4 is only dissolved when being exposed to the circumstance of the small intestine under the action of digestive enzymes such as protease, amylase and the like contained in the small intestine, so as to release the indicator 5 accommodated in the envelope 4. The indicator 5 should be made from a material which is harmless to human bodies, can be absorbed by the body and enables the discharged urine to change color. The indicator 5 of the present invention is preferably a colored contrast agent, which is a biological dye with great biosecurity, being nonirritant and non-toxic to gastrointestinal mucosa and blood of human bodies. The colored contrast agent may be 10-40 mg (1-4 ml) of methylenum coeruleum (methylene blue) which is metabolically characterized in that if injected intravenously it is discharged in urines substantially with no metabolism, and if administrated orally, it is absorbed under the pH condition of the gastrointestinal tract, then is rapidly reduced to white methylenum coeruleum in organisms, and 74% thereof is discharged in urines within 6 days, in which 22% thereof is prototype and the rest is white methylenum coeruleum, with part thereof probably being methylated. A little amount of the methylenum coeruleum is discharged through the bile into feces. Therefore the indicator 5 can be absorbed by the intestinal tract and discharged in urines when being exposed to the circumstance of the intestinal tract.

The cavity of the capsule body of the envelope 4 is filled with the supporting material 1, such that the envelope 4 closely fits against the inner wall of the outer membrane 2, so as to support the outer membrane 2 in a capsule form which has substantially the same size, weight and appearance as those of an common capsule endoscopy. The supporting material 1 should be made from a material soluble in the digestive juices. The supporting material 1 of the present invention is preferably gelatin, lactose or starch which has an adjustable weight ratio so as to stimulate the actual weight of the CE.

Figure 2:
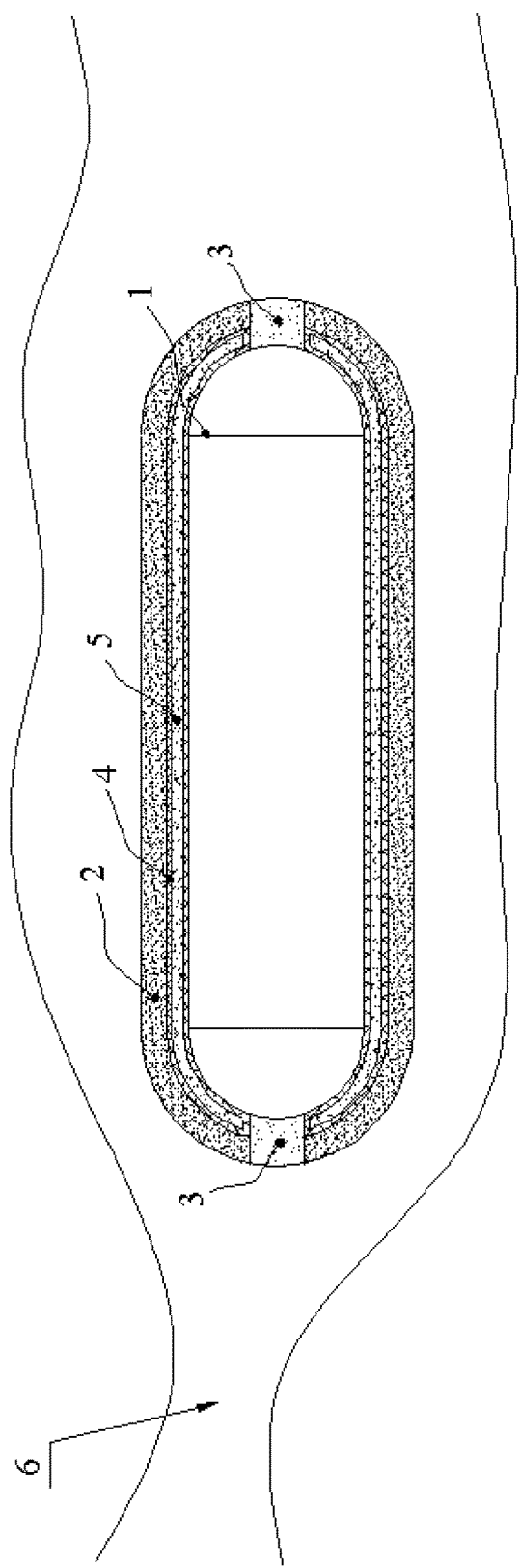
FIG. 2 is a schematic view of the digestive tract patency capsule encountering luminal stenosis in the digestive tract according to the first embodiment of the present invention.

Referring to FIG. 2, when the digestive tract patency capsule according to the first embodiment of the present invention cannot pass through the digestive tract as encountering the luminal stenosis 6 (including stenosis, and obstruction), the digestive tract patency capsule is temporarily incarcerated at this location, and after the dissolution time of the hole plugs 3, the hole plugs 3 are completely dissolved by the digestive juices 7 in the digestive tract, and thus the digestive juices 7 penetrate the outer membrane 2 to contact the envelope 4.

Figure 3:
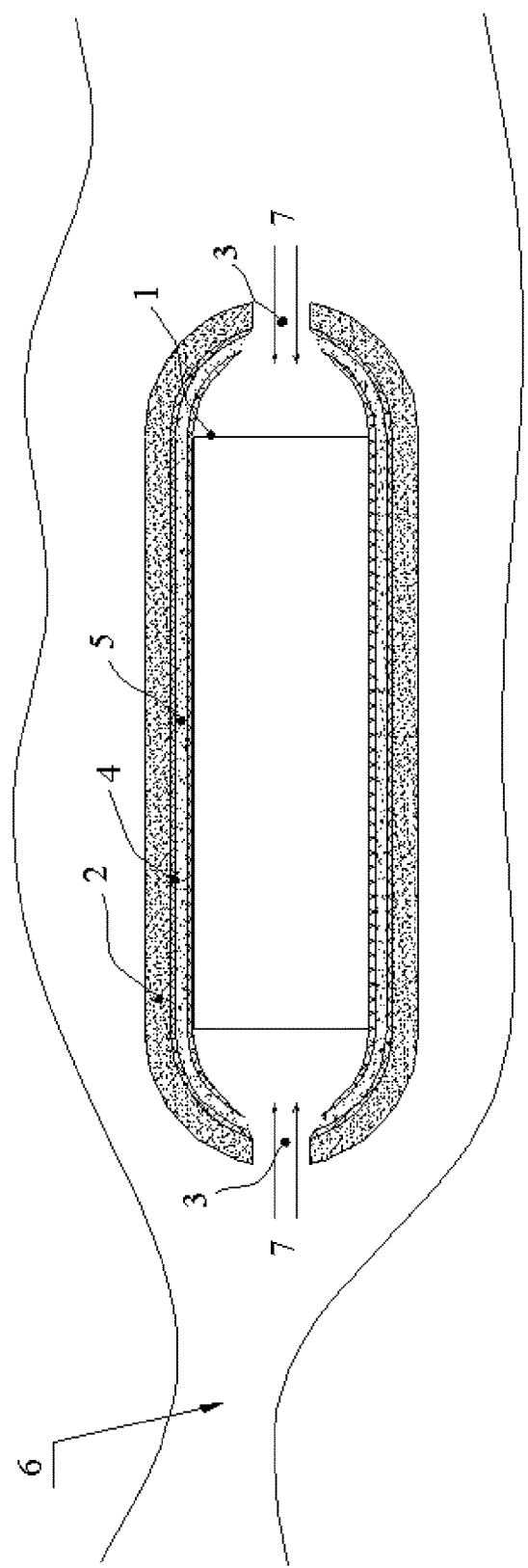
FIG. 3 is a schematic view of the digestive tract patency capsule encountering the luminal stenosis in the small intestine according to the first embodiment of the present invention.

Referring to FIG. 3, the luminal stenosis 6 usually exists in the small intestine, and in such a case, when the digestive juices 7 penetrate the outer membrane 2, on one hand the digestive juices 7 enter the cavity of the capsule body of the envelope 4 via the through holes of the envelope 4 to start the dissolution of the supporting material 1, and on the other hand when the digestive juices 7 contact the envelope 4, the curved end terminal portion of the envelope 4 is dissolved by the digestive juices 7 of the small intestine at the first place, such that the methylenum coeruleum used as the indicator 5 is released from the sealing interlayer of the envelope 4 to the small intestine, which is rapidly absorbed into the blood through the intestinal mucosa, is finally discharged in urines and changes the color of the urine to blue to alarm the user that a stenosis exists in his/her small intestine and thus the CE examination is not feasible.

Figure 4:
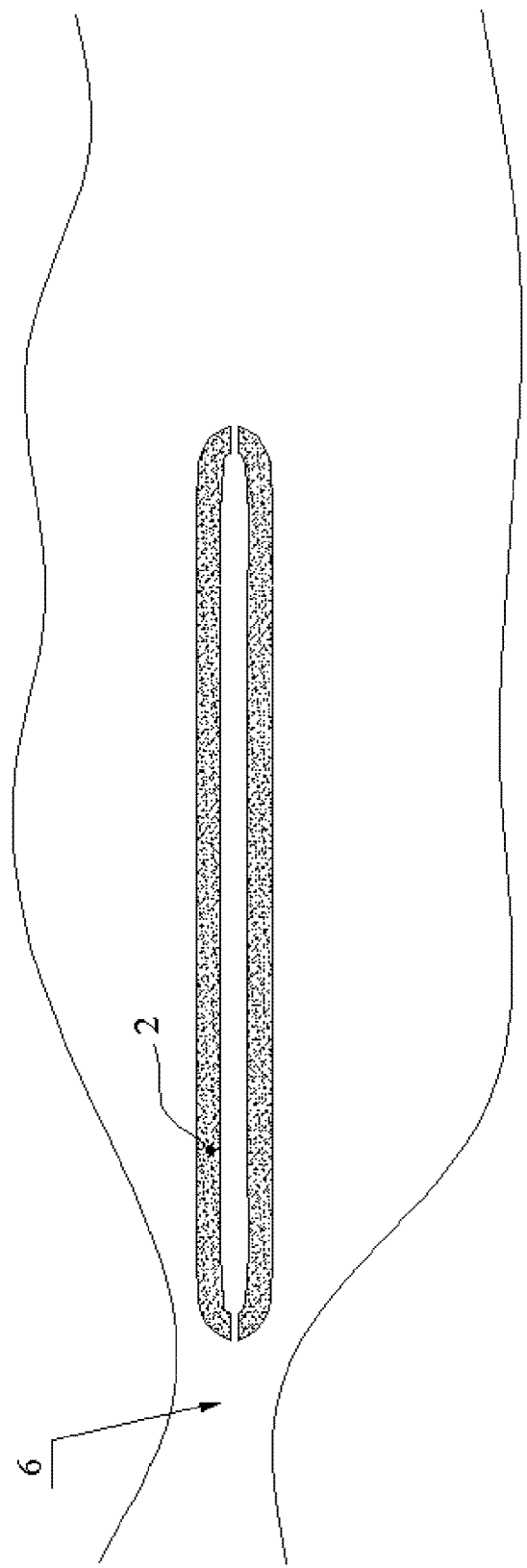
FIG. 4 is a schematic view of the digestive tract patency capsule broken down in the small intestine according to the first embodiment of the present invention.

Referring to FIG. 4, after the indicator 5 is released, finally the supporting material 1 is completely dissolved by the digestive juices 7, and thus the entire digestive tract patency capsule is broken down and the remaining material of the patency capsule passes through the stenosis 6 as an amorphous substance and is finally discharged from the body through the anus.

The following two cases may also be encountered by the digestive tract patency capsule of the first embodiment of the present invention in the digestive tract:

First, if no luminal stenosis exists in the digestive tract, since each of the outer membrane 2 and the hole plugs 3 of the digestive tract patency capsule has a dissolution time greater than the normal emptying time of human digestive tract, in such a case in the digestive tract the digestive tract patency capsule remains the original shape and the structure thereof is stable and intact, so that the actual process of the CE passing through the digestive tract and being discharged through the anus is stimulated.

Second, in a few cases for a user such as a patient with constipation, the mobility of the large intestine is slow, or for very few patients with large intestine obstruction, the digestive tract patency capsule is retained in the large intestine, and after the digestive juices 7 of the large intestine dissolve the hole plugs 3 and then enter the cavity of the capsule body of the envelope 4, since the envelope 4 is not dissolved in the large intestine, the indicator 5 accommodated in the envelope 4 is not released, and also since only the supporting material 1 can be dissolved by the digestive juices 7 of the large intestine, after finally the supporting material 1 is completely dissolved, the capsule structure of the digestive tract patency capsule is broken down while the outer membrane 2 and the envelope 4 remain intact, and the outer membrane 2 and the envelope 4, together with the indicator 5 accommodated in the envelope 4 pass through the stenosis 6 and are finally discharged from the body through the anus.

The Second Embodiment

Figure 5:
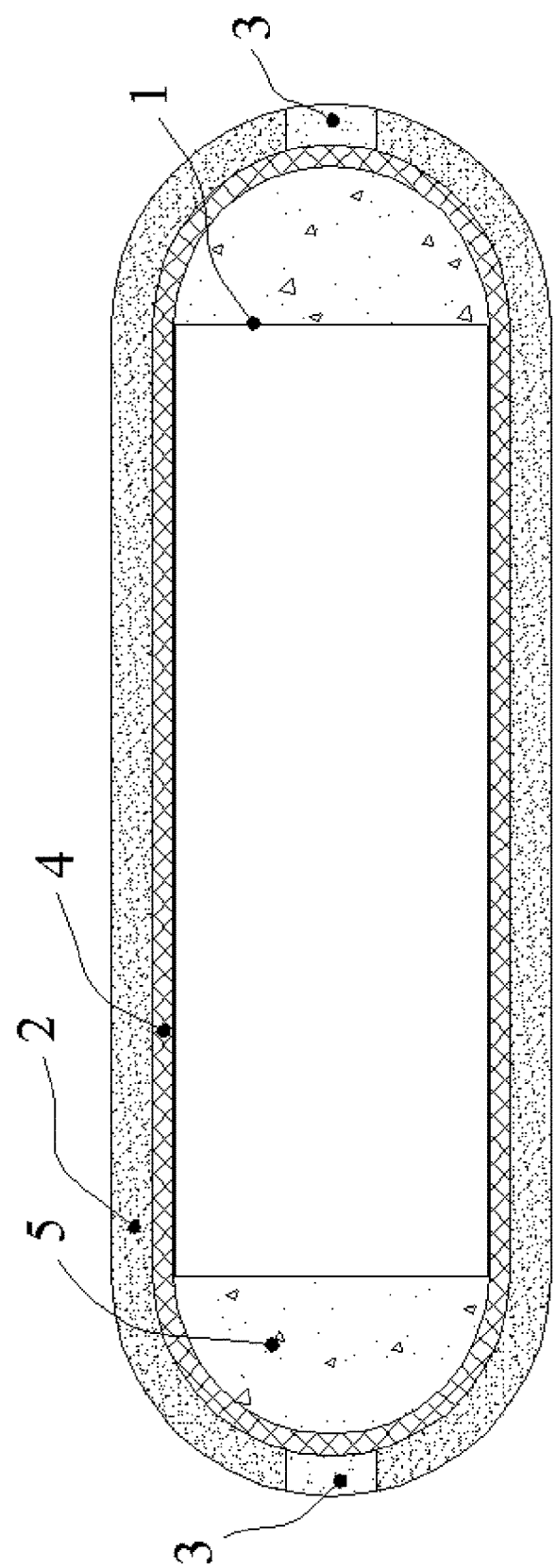
FIG. 5 is a schematic structure view of a digestive tract patency capsule according to a second embodiment of the present invention.

As shown in FIG. 5, the digestive tract patency capsule according to the second embodiment of the present invention is substantially the same as that according to the first embodiment, except that the envelope 4 in the second embodiment is a sealed capsule body having a shape adapted to that of the outer membrane 2, the envelope 4 is installed in the outer membrane 2, the indicator 5 is accommodated in the sealed cavity of the envelope 4, and the sealed cavity of the envelope 4 is filled with the supporting material 1, so that the envelope 4 closely fits against the inner wall of the outer membrane 2, so as to support the outer membrane 2 in a capsule form which has substantially the same size, weight and appearance as those of a common CE.

Figure 6:
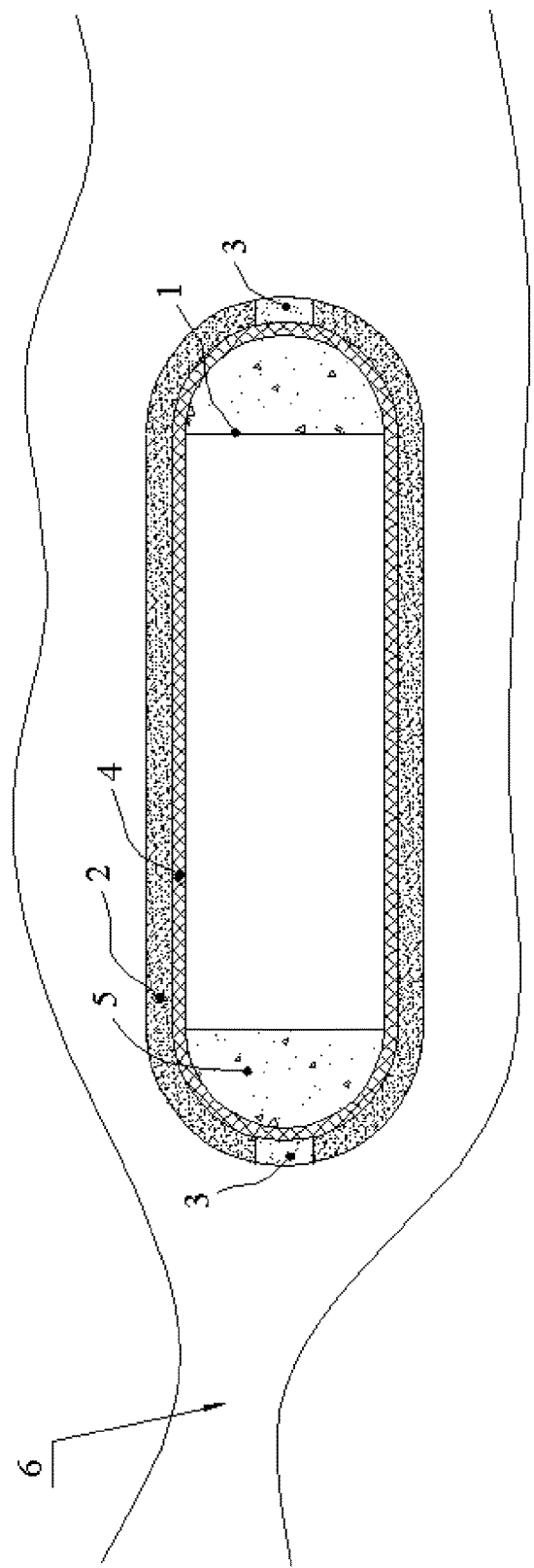
FIG. 6 is a schematic view of the digestive tract patency capsule encountering the luminal stenosis in the digestive tract according to the second embodiment of the present invention.

Referring to FIG. 6, when the digestive tract patency capsule according to the second embodiment of the present invention cannot pass through the digestive tract as encountering the stenosis 6 (including stenosis, and obstruction), the digestive tract patency capsule is temporarily incarcerated at this location, and after the dissolution time of the hole plugs 3, the hole plugs 3 are completely dissolved by the digestive juices 7 in the digestive tract, and thus the digestive juices 7 penetrate the outer membrane 2 to contact the envelope 4.

Figure 7:
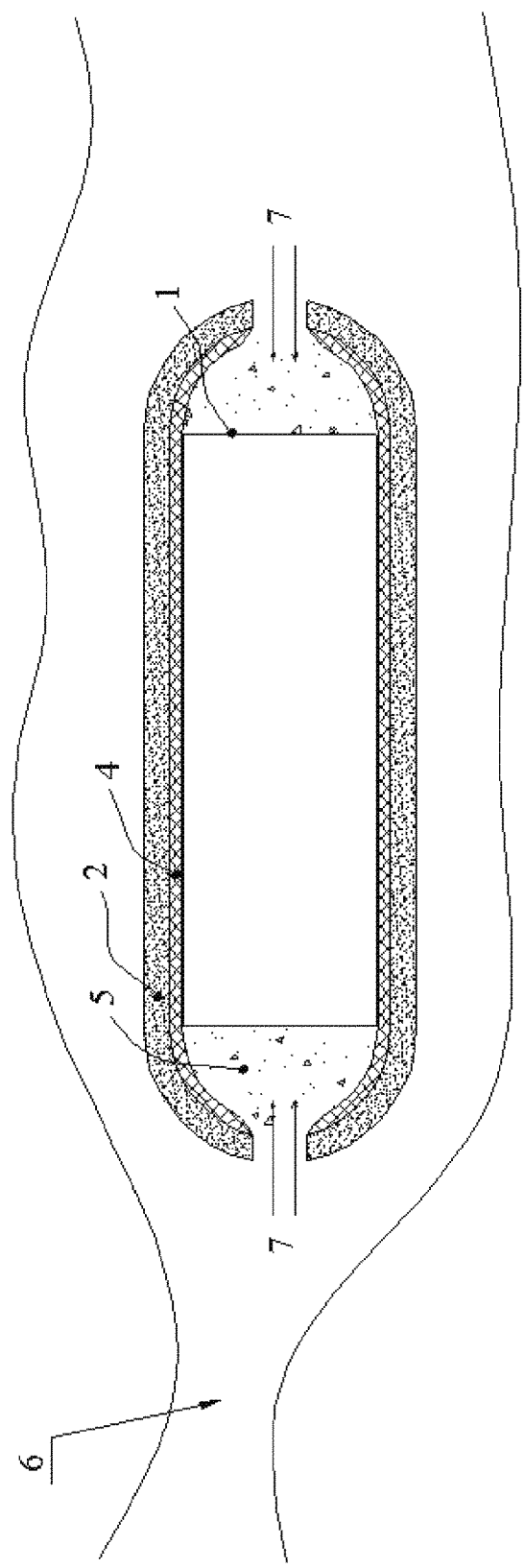
FIG. 7 is a schematic view of the digestive tract patency capsule encountering the luminal stenosis in the small intestine according to the second embodiment of the present invention.

Referring to FIG. 7, the luminal stenosis 6 usually exists in the small intestine, and in such a case, when the digestive juices 7 penetrate the outer membrane 2 to contact the envelope 4, the envelope 4 is dissolved by the digestive juices 7 of the small intestine, and thus the digestive juices 7 further penetrate the envelope 4, such that the methylenum coeruleum used as the indicator 5 is released into the small intestine, which is rapidly absorbed into the blood through the intestinal mucosa, is finally discharged in urines and changes the color of the urine to blue to alarm the user that a luminal stenosis exists in his/her small intestine and thus the CE examination is not feasible.

Figure 8:
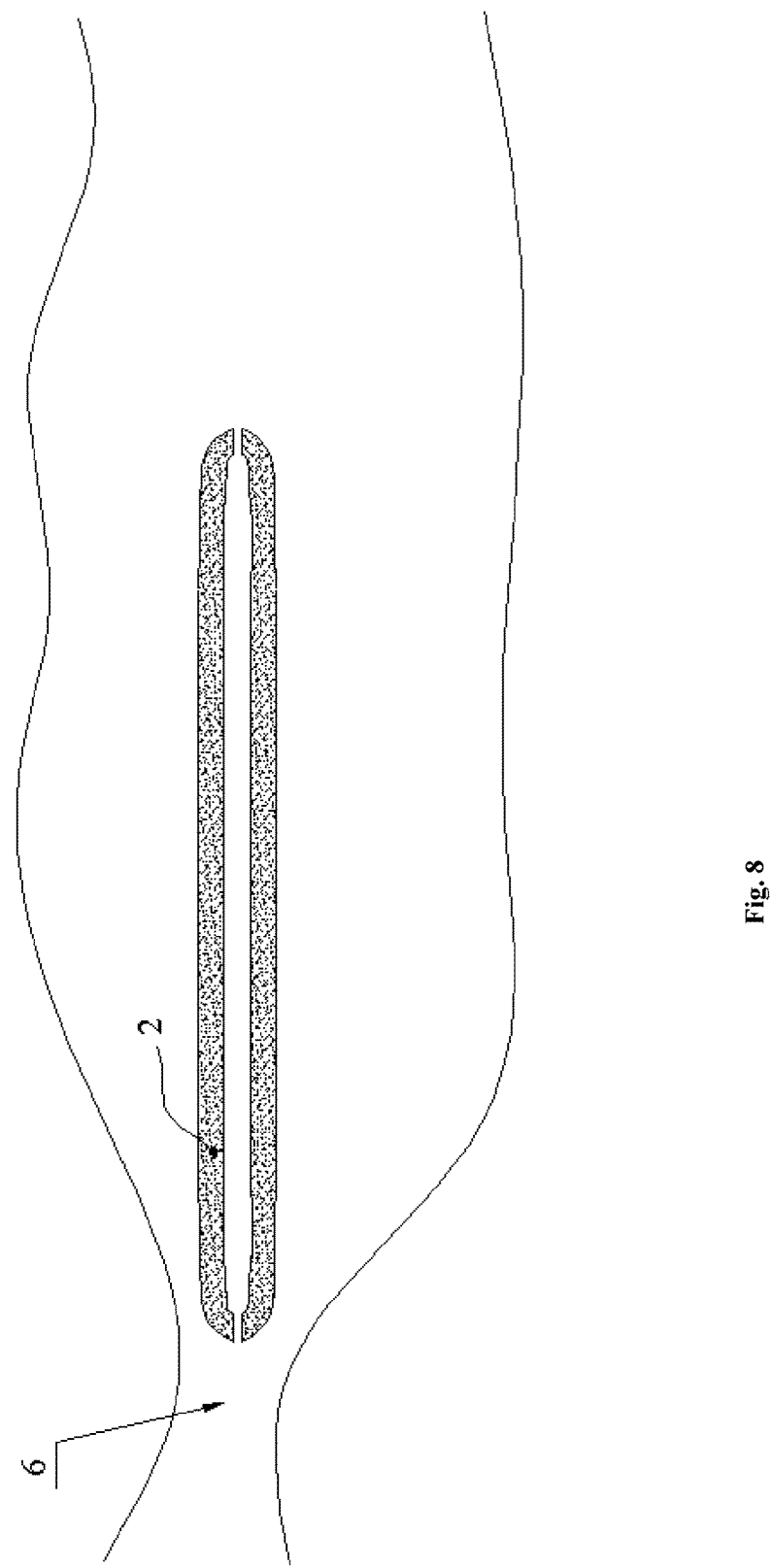
FIG. 8 is a schematic view of the digestive tract patency capsule broken down in the small intestine according to the second embodiment of the present invention.

Referring to FIG. 8, at the same time as the indicator 5 is released, the digestive juices 7 start to rapidly dissolve the supporting material 1, and when the supporting material 1 is completely dissolved, the entire digestive tract patency capsule is broken down and the remaining material of the patency capsule passes through the stenosis 6 as an amorphous substance and is finally discharged from the body through the anus.

The following two cases may also be encountered by the digestive tract patency capsule of the second embodiment of the present invention in the digestive tract:

First, no stenosis exists in the digestive tract, wherein since each of the outer membrane 2 and the hole plugs 3 of the digestive tract patency capsule has a dissolution time greater than the normal emptying time of human digestive tract, in such a case in the digestive tract the digestive tract patency capsule remains the original shape and the structure thereof is stable and intact, so that the actual process of the CE passing through the digestive tract and being discharged through the anus is stimulated.

Second, in a few cases for a user such as a patient with constipation, the mobility of the large intestine is slow and the digestive tract patency capsule is retained in the large intestine, wherein the outer membrane 2 and the hole plugs 3 are dissolved in the large intestine, but since the envelope 4 is not dissolved in the large intestine, the indicator 5 accommodated in the envelope 4 is not released, the envelope 4 and the material accommodated in the envelope 4 are finally discharged through the anus.

Additionally, for very few patients with large intestine obstruction, since the diagnosis that the CE examination is not feasible for such a patient can be obtained from symptoms and examinations thereof, there is no need or allowance to let such a patient to take the digestive tract patency capsule.

Figure 9:
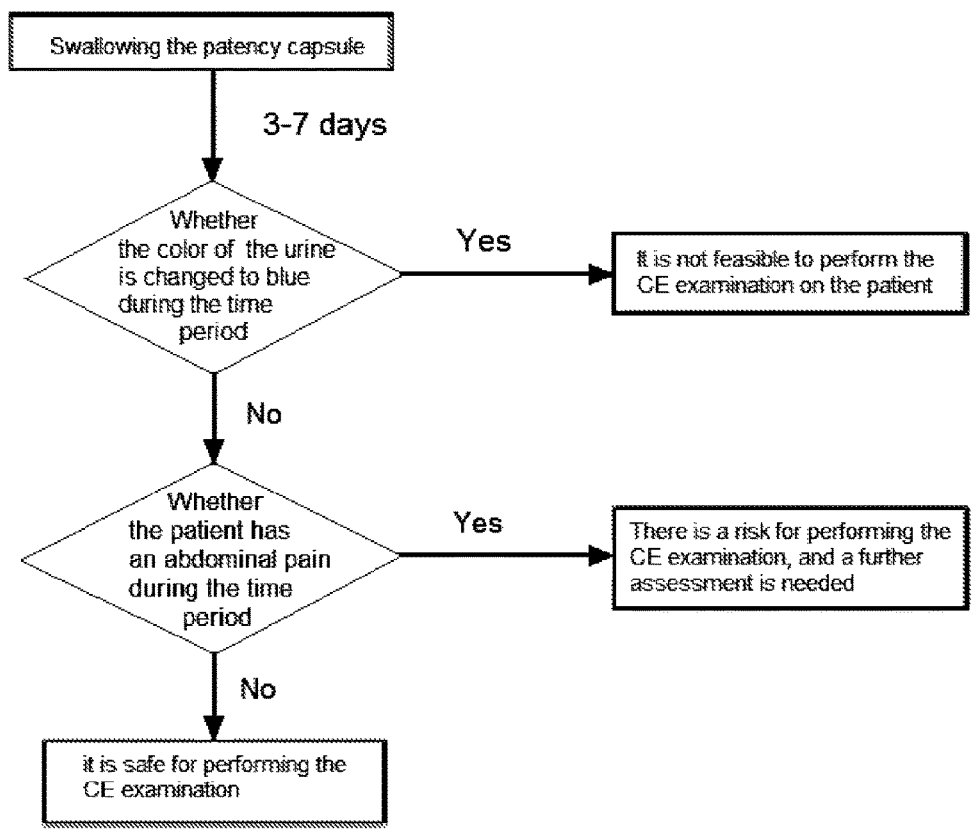
FIG. 9 is a flow block diagram illustrating a digestive tract patency examination performed by using the digestive tract patency capsule of the present invention.

As shown in FIG. 9, an examinee can perform the digestive tract patency examination by himself/herself using the digestive tract patency capsule of the present invention. The examination process is simple and clear, safe and easy, with no need of hospitalization and the guidance of a doctor. The examination process is as follows.

After swallowing the digestive tract patency capsule of the present invention, the examinee works and lives a normal life, with the only requirement of observing whether the color of the urine of the examinee is changed.

After 3-7 days, if the examinee finds that the color of the urine thereof is changed to blue, it can be inferred that the capsule is incarcerated or the capsule is degraded by itself due to a too long transmission time in the digestive tract, and thus it can be judged that the CE examination is not feasible for the examinee.

If the color of the urine is not changed, but within 3 days a new-onset abdominal pain or an aggravated symptom of the original abdominal pain of the examinee emerges, it is inferred that the patient may have the luminal stenosis but the capsule passes through the intestinal tract with difficulty, so that the adverse reaction of the abdominal pain emerges. For this, the risk of performing the CE examination is increased, if the patient insists on performing the examination, the risk should be clearly told to him/her and the examination should be performed under the guidance of a doctor.

If no discomfort of the examinee is observed and the color of the urine is normal, it can be determined that the CE examination can be performed safely.

Furthermore, for the digestive tract patency capsule of the present invention, by omitting the envelope 4, the supporting material 1 and the indicator 5 may also be directly disposed on the outer membrane 2, such that when either the patency capsule is incarcerated in the small intestine or the large intestine, the indicator 5 can be released to function as an alarm to the user that a luminal stenosis exists in his/her small intestine or large intestine.

The present invention is not limited to the aforementioned specific implementations, and based on the disclosure and according to common technical knowledge and conventional means in the art, various forms of equivalent modifications, substitutions or changes as falling within the claimed scope of the present invention can also be made to the present invention, without departing from the aforementioned basic technical idea of the present invention.

What is claimed is:

1. A digestive tract patency capsule, comprising an outer membrane (2) and a supporting material (1) which is soluble in digestive juices, the outer membrane (2) being a sealed soft capsule body made from a sustained-release enteric material, defining a cavity of the capsule body, and having a dissolution time greater than normal emptying time of a human digestive tract, wherein the cavity of the capsule body is provided with an indicator (5) which can be absorbed by human body and change urine color discharged therefrom, and the supporting material (1) is provided in the cavity of the capsule body to maintain the outer membrane (2) in a capsule form: wherein the outer membrane (2) is provided with through holes which are blocked by hole plugs (3) for sealing the outer membrane (2), and the hole plugs (3) are made from a sustained-release enteric material with a dissolution time between normal emptying time of a human digestive tract and the dissolution time of the outer membrane (2); wherein the capsule body comprises two curved end terminals both provided with through holes blocked by hole plugs (3): wherein the material of the outer membrane (2) is polylactic acid, microcrystalline cellulose or polyvinyl pyrrolidone, the material of hole plug (3) is microcrystalline cellulose, glyceryl behenate, polyvinyl pyrrolidone, hydroxypropyl methyl cellulose or lactose, and the hole plugs (3) are adaptively embedded in the through holes and tightly connected to the outer membrane (2) via a biological glue or a UV glue; and wherein the indicator (5) is a colored contrast agent.

2. The digestive tract patency capsule of claim 1, wherein the supporting material (1) is gelatin, lactose or starch and has an adjustable weight ratio so as to simulate the actual weight of a capsule endoscopy.

* * * * *